(12) United States Patent
Oguro et al.

(10) Patent No.: US 6,518,278 B1
(45) Date of Patent: Feb. 11, 2003

(54) CARCINOSTATIC SUBSTANCE FOR COMPATIBLE ADMINISTRATION, PROCESS OF ADMINISTRATING SAME AND PROCESS OF RAPIDLY INSPECTING SAME

(75) Inventors: Masao Oguro, Niigata (JP); Junji Ohnishi, Kanagawa (JP)

(73) Assignee: Debio Pharm S.A., Lausanne (CH)

( * ) Notice: Subject to any disclaimer, the term of this patent is extended or adjusted under 35 U.S.C. 154(b) by 0 days.

(21) Appl. No.: 09/496,603

(22) Filed: Feb. 2, 2000

Related U.S. Application Data

(63) Continuation of application No. 08/862,527, filed on May 23, 1997, now abandoned, which is a continuation of application No. 08/554,935, filed on Nov. 9, 1995, now abandoned.

(30) Foreign Application Priority Data

| Nov. 11, 1994 | (JP) | 6-303015 |
| Dec. 15, 1994 | (JP) | 6-334035 |
| Apr. 18, 1995 | (JP) | 7-116369 |

(51) Int. Cl.$^7$ .................... A61K 31/44; A61K 31/28
(52) U.S. Cl. ........................ 514/283; 514/492
(58) Field of Search .................. 514/492, 283

(56) References Cited

U.S. PATENT DOCUMENTS 5,633,016 A * 5/1997 Johnson .................. 514/283

FOREIGN PATENT DOCUMENTS

| WO | WO 93/09782 | 5/1993 |
| WO | WO 94/12193 | 6/1994 |

* cited by examiner

Primary Examiner—Jerome D. Goldberg
(74) Attorney, Agent, or Firm—Klauber & Jackson

(57) ABSTRACT

Disclosed herein are a process of compatibly administrating a carcinostatic substance with cis-oxalato (1R,2R-diaminocyclohexane) Pt (II), or a certain platinum complex, and a carcinostatic substance which may be employed in the above process. The combination of the carcinostatic substance, for example, 5-fluorouracil and the above platinum complex in accordance with present invention promotes the anticancer property of the carcinostatic substance.

4 Claims, 8 Drawing Sheets

(1) Control (No Carcinstatic Substance)

(2)(3)(4) Control (*l*-OHP or, a large or a small amount of a compatible agent were added at day 1)

(5)(6) *l*-OHP and a compatible agent were added at day 1

(7) to (12) *l*-OHP was added in advance and a compatible agent was added at day 2, day 3 or day 4

(13) to (18) a compatible agent was added in advance and *l*-OHP was added at day 2, day 3 or day 4

CARCINOSTATIC SUBSTANCE FOR COMPATIBLE ADMINISTRATION, PROCESS OF ADMINISTRATING SAME AND PROCESS OF RAPIDLY INSPECTING SAME

This Application is a Continuation of application Ser. No. 08/862,527, filed May 23, 1997 now abandoned which is in turn a Continuation of application Ser. No. 08/554,935, filed Nov. 9, 1995, was abandoned.

BACKGROUND OF THE INVENTION

The present invention relates to a process of compatibly administrating carcinostatic substances and compatibly administrative carcinostatic substances, and especially to a process of compatibly administrating carcinostatic substances in which the synergistic effect appears by compatible administration, compatibly administrative carcinostatic substances employable in the practice of the above process and a mixed carcinostatic substance prepared by mixing these carcinostatic substances. The present invention further relates to a process of rapidly inspecting the carcinostatic substances.

A carcinostatic substance is generally administrated compatibly with another carcinostatic substance for elevating its effectiveness and for preventing tumor cells from obtaining a resistance against a medicine. However, no special method has existed for suitably selecting the administrative substance. The administrative substance has been selected depending on the experience of a clinician under the general considerations on ① an administrative substance is also effective when employed by itself and ② a side effect is not overlapped with that of the administrative substance.

A reaction for restoring from the damage induced by a medicine (carcinostatic substance) is derived in the tumor cell, and if the recovering mechanism is not sufficiently realized, the tumor cell becomes extinct. However, a certain period of time is required for achieving the extinction (necessity of additional administration). When two or more kinds of carcinostatic substances are compatibly employed, a cell biological reaction (synergistic effect) may take place which cannot be recognized in single administration, and in this case the distinct actions of the respective carcinostatic substances (not completely elucidated) may competitively appear. Various administrations conducted under the different conditions such as a dosage of the compatible agents and a dosage time are necessary for elucidating the above mechanism.

The present inventor has developed a reasonable technique in connection with the compatible administration of carcinostatic substances (CANCER CHEMOTHERAPY; Challenge for the Future, vol. 4, 1989; Molecular Biology of DNA Topoisomerases. Proceedings of the International Symposium on DNA Topoisomerases in Chemotherapy, 1991), and proved the effect of the compatible administration of the various carcinostatic substances. However, the combination of the carcinostatic substance which produces the synergistic effect is scarce so that the satisfactorily compatible effect of the carcinostatic substances cannot be easily obtained.

Medicines are roughly divided in accordance with an administration means into two groups one of which is directed to the administration through an intravenous injection and the other is directed to the pororal administration. Most of conventional platinum carcinostatic substances are perorally administered so that a large burden is applied to a patient.

In the meantime, a cell exists from its birth to its death performing various morphological changes especially a nucleic change. It is interesting to monitor the morphological changes in view of molecular biology. In order to conduct this monitoring, a microscope is generally employed so that the condition of the cell is visually observed. However, in this commonly employed microscope observation, the morphological changes inside of the cell cannot be monitored so that the employment of fluorescence dye has been proposed.

However, the fluorescence dye destroys the cell after it is bonded to the cell so that the continuous observation of the morphological changes of the living cell can be impossible even though the morphosis of the cell at the time of employing the fluorescence dye may be observed.

In order to overcome this drawback, the present inventor had investigated various kinds of the fluorescence dye so as to propose 4',6-diamidino-2-phenylindole•2HCl (hereinafter referred to as "DAPI") as fluorescence dye which may be employed for continuously observing the morphological changes of living cells without extinguishing the cells even if it is bonded to the cell [Article in General Meeting of Japan Cancer Institute (July 1990) page 390, 1946).

On the other hand, cell division is an especially interesting phenomenon among the morphological changes, and the the process of the cell division is classified and divided into a division prophase, a division metaphase, a division anaphase and a division telophase. FIGS. 1 to 9 show the conditions of the cell division from the division prophase at the time of initiation of the cell division to the cell division telophase in turn. The left sides of the respective figures are microphotographs of 1500 magnifications of the cell division taken without employing fluorescence dye. Among these, FIGS. 1 to 3 show the cells of the division prophase, FIGS. 4 to 6 show the cells of the division metaphase. FIG. 7 shows the cells of the division anaphase and FIGS. 8 and 9 show the cells of the division telophase.

The cells of FIGS. 1 to 9 are under the conditions of the cell division, but only the cells of FIGS. 6 to 9 can be recognized to be in the cell division through the ordinary microscope observation employing specimens fixed by means of a fixative. The cells of FIGS. 1 to 6 cannot be recognized only through the ordinary microscope observation.

The easy recognition whether the cell is in the condition of the cell division or not is important not only for the scientific purpose but also for the confirmation purpose of the effectiveness of the various medicines.

However, as mentioned, among the several phases of the cell division, the division conditions of the cells in the division prophase and in the period from the first half to the beginning of the second half of the division metaphase cannot be recognized through the ordinary microscope observation so that the detailed study thereof is impossible.

Frequent occurrence of the various organ cancers invites vital developments of anti-tumor substances or carcinostatic substances, and in these developments, it is essential to rapidly conduct the inspection of the effectiveness of the carcinostatic substances (sensibility test) for reducing the development expenses.

The above inspection test is roughly divided into two methods. A first method essentially consists of cultivating tumor cells, cultivating the tumor cells in a test tube with carcinostatic substances and judging the degree of the extinction after the extinction of the cells, and a second method essentially consists of injecting or perorally administrating carcinostatic substances to an animal transplanted with tumor cells and comparing the numbers of survival days of the animals for judging the effectiveness of the carcinostatic substances.

The judgment of the effectiveness of the carcinostatic substances cannot be performed before the extinction of the cells of the death of the animals in each of the above methods and between one and four weeks are ordinarily required for the judgment so that not only the rapid judgment is impossible but also the expenses for continuing the test increase.

Although the present inventor has proposed a method of more rapidly inspecting the effectiveness of medicines (Japanese patent laid open gazette No. 58-184547), not less than four days and between seven days and four weeks are required in the test tube method and in the animal method, respectively, for the judgment.

Further in these methods, only the effectiveness of medicines or the extinction effect is made clear and how the carcinostatic substance functions to extinct the cancer cells (mechanism) cannot be specified.

Although the above method employing DAPI as fluorescence dye has enabled the visual observation of the process of cell extinction by means of the carcinostatic substance while keeping the cells alive, the effectiveness of the carcinostatic substance cannot be confirmed without the observation of the cell extinction in the said process so that between three and six days are required.

SUMMARY OF THE INVENTION

In view of the above drawbacks, an object of the present invention is to provide a process of compatibly administrating cis-oxalato (1R,2R-diaminocyclohexane) Pt (II) (hereinafter referred to as "l-OHP") which is a new carcinostatic substance with one or more existing carcinostatic substances.

Another object of the present invention is to provide the above process in which the optimum combination of the carcinostatic substances is proposed.

A further object of the present invention is to provide a process of compatibly administrating a new platinum complex with one or more existing carcinostatic substances for further elevating the anticancer property of a carcinostatic substance a main component of which is the above platinum complex.

A still further object of the present invention is to provide a process of easily distinguishing cells not only in the division anaphase and the division telophase in the cell division but also in the division prophase and the division metaphase and of observing their morphosis.

A still further object of the present invention is to provide a process of inspecting the effectiveness of carcinostatic substances utilizing the above process of distinguishing the cells.

A first aspect of the present invention is a process of compatibly administrating a carcinostatic substance which comprises compatibly administrating one or more compatible agents selected from a group consisting of cisplatin, carboplatin, 5-fluorouracil (hereinafter referred to as "5-FU"), tegaful, carmoful, doxifluridine, uracil, irinotecane, adriamycin, etoposide, mitomycin, mitoxisantrone and bleomycin with l-OHP.

A second aspect of the present invention is a carcinostatic substance selected from a group consisting of cisplatin, carboplatin, 5-FU, tegaful, carmoful, doxifluridine, uracil, irinotecane, adriamycin, eloposide, mitomycin, mitoxantrone and bleomycin which can be compatibly administrated with l-OHP. This carcinostatic substance may prepared by simply mixing the cisplatin or the like and the l-OHP or by making a coordination bond between them.

A third aspect of the present invention is a process of compatibly administrating a carcinostatic substance which comprises compatibly administrating one or more compatible agents selected from a group consisting of cisplatin, vincristin, carboplatin, 5-FU, tegaful, carmoful, doxifluridine, uracil, irinotecane, adriamycin, etoposide, mitomycin, mitoxantrone and bleomycin with a platinum complex having a Formula I [in this Formula, a Formula II is a diamine selected from a group consisting of 1,2-cycloalkane ($C_5$ to $C_7$) diamine {its stereostructure is cis-(R,S-), trans-d(1S,2S-) or trans-l (1R,2R-)} having a Formula III, 2-aminomethlcyclohexylamine {its stereostructure is cis-l (R,R-), cis-d(S,S-), trans-l (R,S-) or trans-d(S,R-)} having a Formula IV and 1,1-diaminomethylcyclohexane, 0-phenylenediamine, ethylenediamine or propyrenediamine having a Formula V, and a Formula VI is a ligand forming a five or six-membered ring coordinated to Pt(IV) in 0—0 coordination, and X is an aliphatic alkyl or an aromatic alkyl having $C_1$ to $C_{10}$].

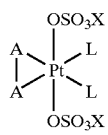

Formula I

Formula II

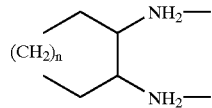

Formula III

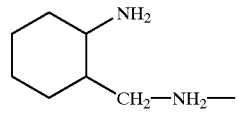

Formula IV

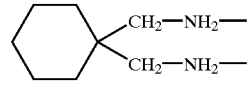

Formula V

Formula VI

A fourth aspect of the present invention is a carcinostatic substance comprising the compatible agent and the platinum complex of the third aspect.

A fifth aspect of the present invention is a process of observing cell division which comprises adding fluorescence dye to cells to be observed, bonding the fluorescence dye to each cell, and observing the cells with a microscope of clarifying the cell division condition.

A sixth aspect of the present invention is a process of rapidly inspecting a carcinostatic substance which comprises adding fluorescence dye and a carcinostatic substance to be inspected to a plurality of cancer cells which have been cultivated, continuing the cultivation, measuring the number of the cells in the division period appearing in the plurality of the cancer cells and inspecting the effect of the carcinostatic substance.

In accordance with the first aspect of the present invention, a shown in the below Examples, the compatible administrations of the l-OHP and the existing carcinostatic substances to the tumor cells exhibit. In almost all the cases, an additive effect of extinguishing the tumor cells and, in the most cases, exhibit a synergistic effect.

The increase of the extinguishing effect of the tumor cells obtained by the compatible administration of the carcinostatic substances is significantly meaningful especially in the range competing with the multiplication rate of the tumor cells, and even a slight increase of the extinguishing effect may largely promote the therapeutic effect.

The increase of the extinguishing effect in accordance with the above process of compatibly administrating the carcinostatic substances is made to be epoch-making by suitably selecting the combination of the carcinostatic substances so that this process can considerably contribute to the most cancer therapies.

The l-OHP and the compatible agent may be simultaneously administrated or either of them may be added later than the other, and the timing of the administration may be determined depending on the combination.

However, in order to reduce the burden of a patient and a physician, the simultaneous administration is desirable, and the 5-FU of which an effect produced by its simultaneous administration is twice an expected value is an especially effective compatible agent.

The compatibly administrative carcinostatic substance in accordance with the second aspect possess the remarkable therapy effect against the cancer as mentioned in connection with the first aspect.

In case of the combination of the carcinostatic substances preferably administrated simultaneously, desirably a pellet may be formed or an injection ampoule may be prepared with the mixture of the l-OHP and one or more compatible agents because the labor of the compatible administration may be omitted.

In accordance with the third aspect of the present invention similar to the first aspect, the compatible administrations of the platinum complex having a Formula VII and the existing carcinostatic substances to the tumor cells exhibit, in almost all the cases, an additive effect of extinguishing the tumor cells and, in the most cases, exhibit a synergistic effect.

The compatibly administrative carcinostatic substance in accordance with the fourth aspect possesses the remarkable therapy effect against the cancer as mentioned in connection with the third aspect.

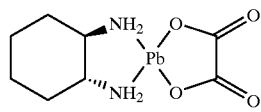

Formula VII

The fifth aspect of the present invention enables the visual observation of the divided cells under the division prophase and the division metaphase which are difficult to be visually observed by adding the fluorescence dye which can be bonded to ordinary cells and cancer cells under the cultivation and bonding the dye to the said cells, and in other words, enables the observation not only for of the shape of the divided cell but also of the change of a chromosome so that the observation of the said divided cell under the division prophase and the division metaphase in which an external change may seldom occur becomes possible.

In accordance with this observation method, the number of the cells under the cell division among a plenty of cells can be accurately counted so that a percentage of the cells under the cell division to all the cells can be calculated.

If the carcinostatic substance to be inspected exhibits the same number of the cells under the cell division as that of a control having no carcinostatic substance, the said carcinostatic substance to be inspected possesses no anti-tumor property. If, on the other hand, the said substance exhibits the smaller or larger number than that of the control, the carcinostatic substance to be inspected possesses the anti-tumor property so that the effectiveness as the carcinostatic substance can be judged by counting the number of the cells under the cell division and comparing the number with that of the control.

BRIEF DESCRIPTION OF DRAWINGS

FIGS. 4 to 6 are microphotographs of 1500 magnifications of cells in cell division metaphase.

FIG. 7 is a microphotograph of 1500 magnifications of cells in cell division anaphase.

FIGS. 8 and 9 are microphotographs of 1500 magnifications of cells in cell division telophase.

In FIGS. 1 to 9, the left hands thereof are those without fluorescence dye and the right hands are those with fluorescence dye.

DETAILED DESCRIPTION OF THE INVENTION

Figure 1:
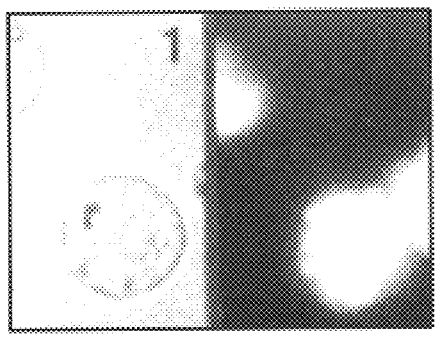
FIGS. 1 to 8 are microphotographs of 1500 magnifications of cells in cell division prophase.
Figure 4:
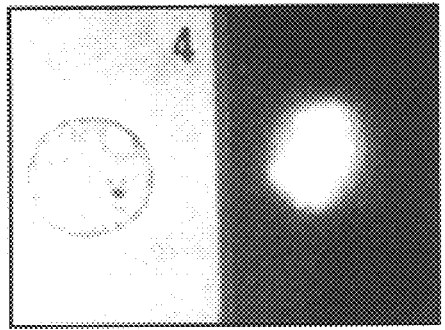
Figure 2:
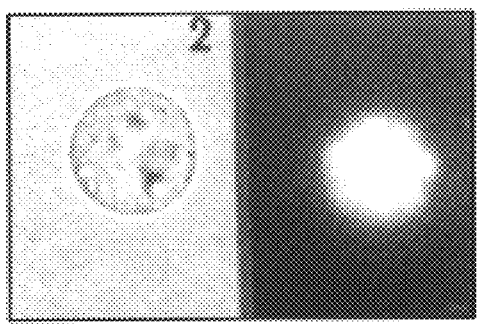
Figure 5:
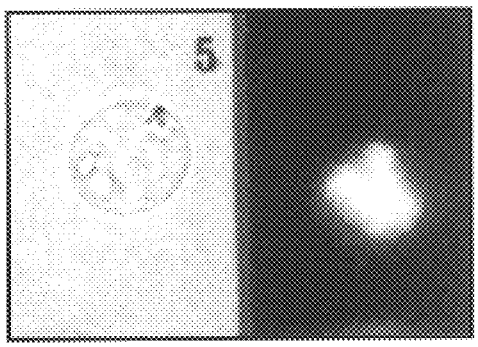
Figure 3:
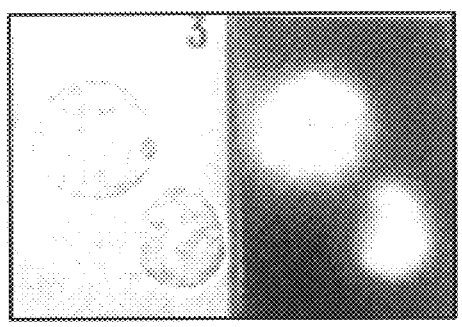
Figure 6:
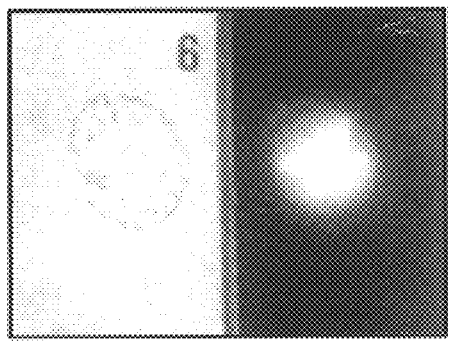
Figure 7:
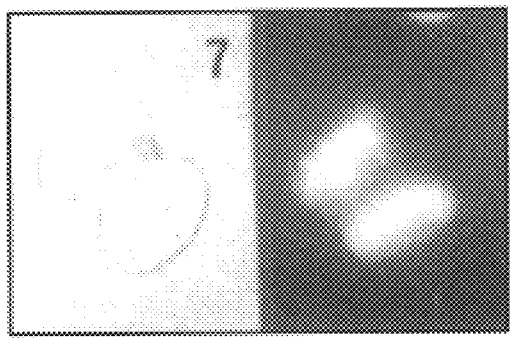
Figure 8:
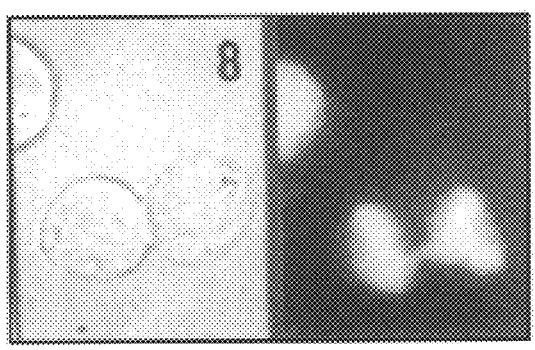
Figure 9:
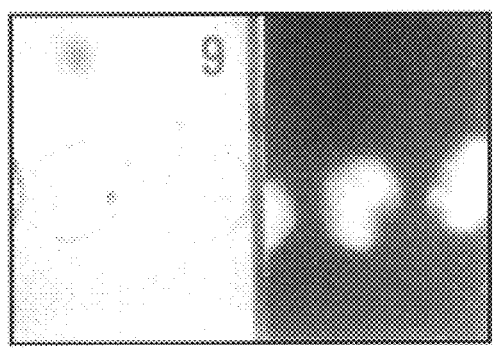

The multiplication rate of tumor cells is higher than that of an ordinary cell so that if the extinction effect of the carcinostatic substance against the tumor cells is substantially the same as or lower than the multiplication rate, the said substance can only depress the progress of the cancer and the fundamental therapy cannot be expected. The carcinostatic substance possesses its own optimum dosage and even if a larger amount of the carcinostatic substance than the optimum dosage is administrated, the extinction effect does not proportionally increase and only a slight increase is expected. Moreover, an adverse effect due to the the damages of the ordinary cells induced by the large dosage appears more severely so that the increase of the therapeutical effect by means of the large dosage of the single carcinostatic substance is seldom expected.

The compatible administration of the carcinostatic substances conventionally conducted broadens the possibility of cancer therapy by overcoming the limitation of the large dosage of the single carcinostatic substance. Although the mechanism is not sufficiently elucidated, the employment of the specific combination may introduce the possibility of remarkably increasing the extinction effect of the tumor cells. That is, the employment of a carcinostatic substance A and a carcinostatic substance B may produce an effect which equals to a total of an extinction effect of the employment of the single carcinostatic substance A and of an extinction effect of the employment of the single carcinostatic substance 8 (additive effect) or which is larger than the above total effect (synergistic effect).

The carcinostatic substance is insufficient only for depressing the progress of the cancer and the complete extinction of the tumor cells is desirable. For achieving this extinction, it is required to extinct the tumor cells more rapidly than the multiplication rate of the tumor cells, and theoretically the tumor cells eventually extinct completely even when the extinction rate of the tumor cells by means of the carcinostatic substance is slightly larger than the multiplication rate thereof. However, due to the danger of the transfer of the tumor cells and of the administration of the toxic carcinostatic substance to a patient for a long period of time, the realization of a carcinostatic substance which can extinguish the tumor cells in a short period of time has been requested. For achieving this realization, the combination of two or more carcinostatic substances synergistically increasing the extinction effect of the tumor cells is essential, and the appearance of the combination of the carcinostatic substances having the synergistic effect decisively contributes to the current cancer chemotherapy.

Although the mechanism of extinguishing the tumor cells by means of the compatible administration of the carcinostatic substances has not yet been completely elucidated, the administration effects at the respective stages after the compatible administration or the effects depending on the time after the compatible administration enable to provide new strategic information regarding the extinction of the tumor cells which cannot be conventionally produced by simply confirming the life and the death of the tumor cells.

The first and second aspects of the present invention propose the combination of the carcinostatic substances especially having the synergistic effect or at least having the additive effect, and employ l-OHP having a Formula I as a target carcinostatic substance which is compatibly administrated with one or more existing carcinostatic substances. The compatible administration synergistically or additively elevates the anticancer properly of the l-OHP.

The present inventors have tried to measure the extinction effects of tumor cells produced by the compatible administration of 15 kinds of the existing carcinostatic substances (compatible agents) including cisplatin, carboplatin, 5-FU, tegaful, carmoful, doxifluridine, uracil, irinotecane, adriamycin, etoposide, mitomycin, mitoxantrone, bleomycin, vincristin and vindecin and of the l-OHP (target agent, Formula VII). An administration method (simultaneous administration, addition

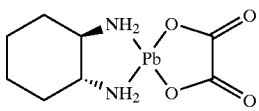

Formula VII administration) and a dosage (large amount administration, small amount administration) have been also investigated in addition to the simple compatible administration.

In the evaluation of the extinction effect of the tumor cells of the respective combinations, a pure extinction effect produced by the compatible administration of the compatible agent and the l-OHP is calculated by subtracting an extinction effect of a control (no carcinostatic substance is employed).

The compatibly administration effect is calculated by employing an Equation ① described later. When the value (%) calculated by this Equation is between 85 and 115%, the compatible administration effect is evaluated to be an additive effect. When the value is below 85%, it is evaluated to be below the additive effect. When the value is over 115%, it is evaluated to be a synergistic effect, ±15% is a reliability limit or a measurement error.

As a result, as described in detail later, the eight compatible agents, that is, cisplatin, 6-FU, irinotecane, adriamycin, etoposide, mitomycin, mitoxantrone and bleomycin produce the additive effect or the synergistic effect regardless of the administration method and the dosage in almost all the cases. Especially, the compatible effects of the cisplatin and the 5-FU are remarkable and the combination of the 5-FU and the l-OHP is most appropriate. On the other hand, the two compatible agents, that is, vincristin and vindecin produce the additive effect at best.

In the compatible administration of the cisplatin and the l-OHP, the synergistic effects can be obtained in all the cases when the cisplatin and the l-OHP are simultaneously administrated and the l-OHP is administrated before the cisplatin, and depending on the conditions, the extinction effects of the tumor cells are twice the expected value (additive effect).

In the compatible administration of the 5-FU and the l-OHP, the synergistic effects can be obtained in almost all the administration conditions regardless of the administration method and the dosage of the 5-FU, and similarly to the above case of the cisplatin, the extinction effect of the tumor cells twice the expected value can be obtained depending on the conditions. Among the compatible agents investigated, the most excellent effect can be obtained in the above combination, and the 5-FU is most recommendable as the compatible agent with the l-OHP.

In the compatible administration of the irinotecane and the l-OHP, the synergistic effects can be obtained in all the combinations when the l-OHP is added later.

In the compatible administration of the adriamycin and the l-OHP, the synergistic effects can be obtained in almost all the combinations when the l-OHP is added later.

In the compatible administration of the etoposide and the l-OHP, the synergistic effects can be obtained in almost all the combinations when the l-OHP is added later.

In the compatible administration of the mitomycin and the l-OHP, the synergistic effects can be obtained in most combinations when the l-OHP is administrated before to the mitomycin.

In the compatible administration of the mitoxantrone and the l-OHP, the synergistic effects can be obtained in all the combinations when a small amount of the mitoxantrone is employed and the l-OHP is added later.

In the compatible administration of the bleomycin and the l-OHP, the synergistic effects can be obtained in most combinations when the l-OHP is added later at a third day and a fourth day.

The effect the same as or slightly inferior to that of the cisplatin and of the 5-FU is expected to be obtained in the carboplatin, the tegaful, the carmoful, the doxifluridine and the uracil. The compatible effect of the l-OHP and a single medicine of the 5-FU or composition (mixture of the tegaful and the uracil) is also expected to be similar to that of the 5-FU and the l-OHP.

Two or more of these effective compatible agents may be employed compatibly with the l-OHP as well as one compatible agent is employed singly with the l-OHP, and a further effect can be expected by the former compatible administration.

In the compatible administration of the vincristin and the l-OHP, no synergistic effects can be obtained in all the combinations and the additive effects can be obtained in most combinations.

In the compatible administration of the vindecin and the l-OHP, no synergistic effects can be obtained in all the 14 combinations and the additive effects can be obtained in only three combinations so that the vindecin is worst among the compatible agents inspected.

As mentioned, the compatible effect is affected not only by the kind of the compatible agent but also by the dosage and the timing of the administration. Although no apparent standard in connection with the dosage exists, the apparent influence of the timing of the administration is applied to the effect of the respective compatible agents. While the effect about twice the expected value is obtained in most cases when the l-OHP administration is preceded and the cisplatin is added later, the synergistic effect is obtained only in one combination and the effect below the synergistic effect is obtained in three combinations when the cisplatin administration is preceded.

When a medicine is administrated to a patient, the simultaneous administration is more preferable than the time lag administration because the burden to the patient and a physician is larger in the time lag administration. The 5-FU produces the effect of 180% or 150% of the expected value in the simultaneous administration, and it is apparent in this respect that the combination of the 5-FU and the l-OHP is preferable. In the present invention, the simultaneous administration includes a case wherein a plurality of carcinostatic substances are simultaneously administrated with no time lag and another case wherein a plurality of carcinostatic substances are continuously administrated with a slight time lag by means of separate administration procedures, and the other cases are included in the time lag administration.

Although, in the below Examples of the first and second aspects of the present invention, the compatible administration was conducted only to tumor cells of leukemia, it is expected that the administration process and the mixed carcinostatic substance can exhibit the synergistic effect and the additive effect to other organ cancers.

The administration of the carcinostatic substance can be conducted perorally or through an injection, a vagina, an anus or the application to a skin. When the effect is produced by the simultaneous administration of the l-OHP and the compatible agent, the both agents may be mixed and made to be a tablet or may be enclosed in an injection ampoule. Other than the mixing, the l-OHP and the compatible agent may be integrated by means of a chemical bond and added to the tablet or enclosed in the ampoule. When the time lag administration is preferable, the l-OP and the compatible agent are separately prepared and one of them is at first administrated and the other is added later.

In accordance with the third and fourth aspects of the present invention, the combination of carcinostatic substances having at least the additive effect is proposed in which a platinum complex having a Formula I is employed as a target carcinostatic substance and administrated compatibly with one or more existing carcinostatic substances. The anticancer effect of the platinum complex is elevated synergistically or additively by means of the compatible administration so that the much contribution to the cancer therapy by means of the compatible administration is expected.

In the Formula I, a Formula II is a diamine selected from a group consisting of 1,2-cycloalkane ($C_5$ to $C_7$) diamine {its stereostructure is cis-(R,S-), trans-d(1S,2S-) or trans-l (1R,2R-)} having a Formula III, 2-aminomethylcyclohexylamine (its stereostructure is cis-l (R,R-), cis-d(S,S-), trans-l(R,S-) or trans-d(S,R-)} having a Formula IV and 1,1-diaminomethycyclohexane, O-phenylenediamine, ethylenediamine or propyrenediamine having a Formula V, and a Formula VI is a ligand forming a five or six-membered ring coordinated to Pt(IV) in O—O coordination, for example, a Formula VII, a Formula IX, a Formula X, a Formula XI, a Formula XII and a Formula XII, and X is an aliphatic alkyl or an aromatic alkyl having $C_1$ to $C_{10}$].

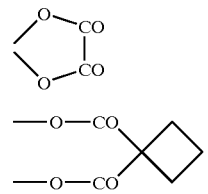

Formula VIII

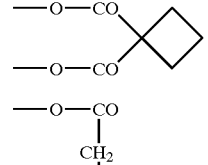

Formula IX

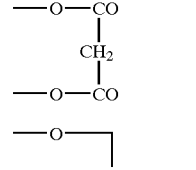

Formula X

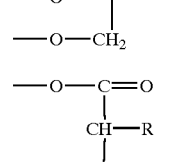

Formula XI

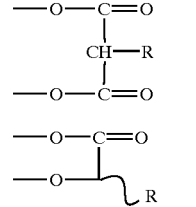

Formula XII

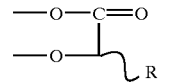

Formula XIII

In the present invention, the measurement of the extinction effects of tumor cells produced by the compatible administration of the existing carcinostatic substances (compatible agents) including cisplatin, carboplatin, 5-FU, tegaful, carmoful, doxifluridine, uracil, irinotecane, adriamycin, etoposide, mitomycin, mitoxantrone, bleomycin, vincristin and vindecin and of the platinum complex (target agent) is tried.

The evaluation is conducted in accordance with the same procedures of the above first and second aspects.

As a result, it is clarified that the synergistic effect is obtained by the compatible administration of the platinum complex with the cisplatin or with the vincristin.

In the fifth and sixth aspects of the present invention, fluorescence dye which is bonded to cells without extinguishing the cells to generate fluorescence is employed. As the said fluorescence dye, the above DAPI can be employed. Although the DAPI itself is known, the use for the observation of the cell division while keeping the cells alive is unknown. The present inventors have investigated such fluorescence dye as Hoechst 33258, acridine orange and acridine yellow other than the DAPI. Their toxicity is too strong to keep the cell alive.

When the DAPI which is fluorescence dye is cultivated with ordinary or cancer cells, the DAPI is bonded to the nucleus of the cell to generate fluorescence. The cell bonded with the DAPI more clarifies the state of the cell nucleus at the time of cell division. The right hand sides of FIGS. 1 to 9 are microphotographs of the cells bonded with the DAPI under the same states of the cell division as those of the left hand sides of FIGS. 1 to 9 in which the cells are not bonded with the fluorescence dye.

In the right hand microphotographs of FIGS. 1 to 9, the cell states not only in the latter part of the division metaphase (FIG. 6), in the division anaphase (FIG. 7) and in the division telophase (FIGS. 8 and 9) but also in the division prophase (FIGS. 1 to 3) and from the beginning to the middle of the division metapase (FIGS. 4 and 5) can be recognized by means of the fluorescence.

While only the morphosis change accompanied with the external change of the cell can be observed with the ordinary microscope, the cell in the division prophase and in the division metaphase which is not accompanied with the external changes can be observed and recognized in accordance with the fifth aspect of the present invention because the chromosome division in the living cell is also recognized.

Then a process of inspecting a carcinostatic substance utilizing the above process of observing the cell division will be described.

A first reason why a tumor or a cancer cell is malignant is that the cancer cell freely multiplies. Accordingly, if the administration of the carcinostatic substance ceases the multiplication of the cancer cells, it means that the administrated substance actually functions as a carcinostatic substance.

After over a certain number of cancer cells are prepared by cultivation, a carcinostatic substance is added to the cancer cells. The number of the cells under the cell division at the respective measuring times is counted while continuing the cultivation. Since the cell division does not occur continuously and, for example, it occurs once in a day about for 30 minutes, the single counting of the divided cells cannot accurately judge the effectiveness of the carcinostatic substance. Accordingly, the effectiveness of the carcinostatic substance can be inspected by counting the number of the cells under the cell division among a certain number (for example, one thousand) of cells several times, comparing the said number with that of the former counting or the previous counting thereof and grasping the progress of the cell division by means of the increase or the decrease of the above comparison.

If the DAPI is added with the carcinostatic substance during this procedure, the accurate counting of the number of the divided cells can be performed because the cells under the any phase of the cell division can be recognized.

When the number of the divided cells decreases as a result of the comparison between the measurement values, it is judged that the multiplication of the cancer cells is depressed, or the function of the carcinostatic substance is performed. When, on the other hand, the number of the divided cells increases compared with the control, a certain function of the carcinostatic substance is judged to be performed.

While the administration of the carcinostatic substance depresses the cell division because the ordinary carcinostatic substance functions to depress the cell division, a certain carcinostatic substance functions to depress the further division of the cells under the cell division to cease the multiplication of the cells under the cell division to exhibit its anti-tumor property. In case of this carcinostatic substance, the number of the cells under the cell division increase proving the existence of the anti-tumor property.

EXAMPLES

Although Examples of the present invention will be described, these Examples are not construed to restrict the present invention.

Example 1

Figure 10:
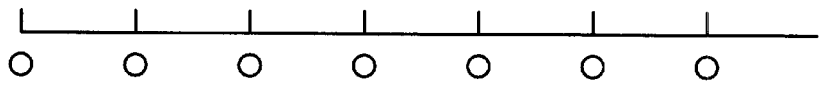
FIG. 10 is a diagram showing a timing schedule of compatible administration of compatible agents and l-OHP in Example 1.
Figure 10:
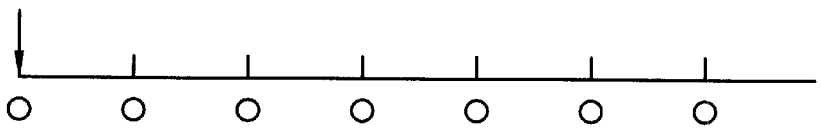
Figure 10:
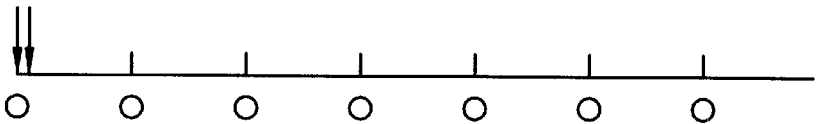
Figure 10:
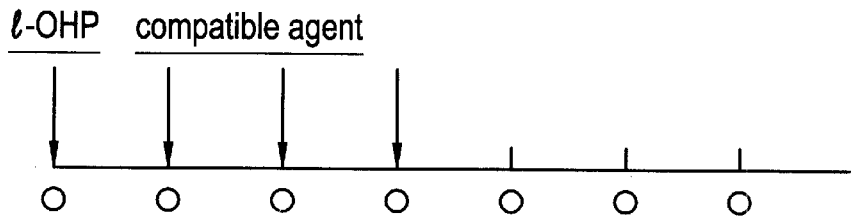
Figure 10:
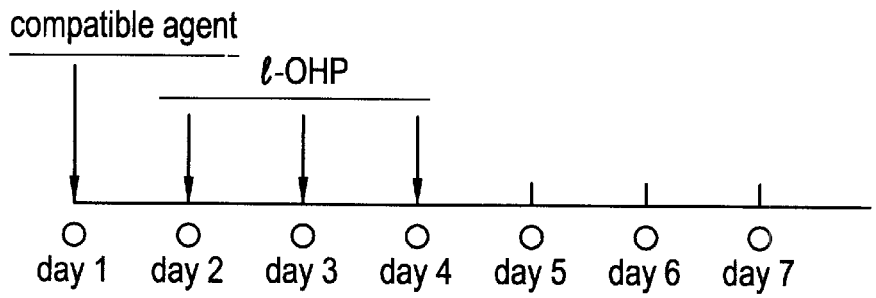

A target tumor cell was a human leutecyte strain cell (RPMI-8402 of Gibuko K.K.). To these cells was added blood serum of a cow embryo (15%, Gibuko K.K.) to prepare a cell floating liquid of which the number of the cells was $10^6$/ml in a cultivation bottle (tradename; Sumiron of Sumitomo Bakelite o., Ltd.) having a volume of 6 ml. A plenty of the cultivation bottles having the cell floating liquid therein were prepared, and the following experiments were conducted while selecting one kind of a compatible agent among cisplatin, 5-FU, irinotecane, adriamycin, etoposide, mitomycin, mitoxantrone, bleomycin, vincristin and vindecin. The time schedules of the controls (no addition of medicines, addition of only the 1-OHP and addition of only a compatible agent, and specified in the below items (1) to (4)) and of the compatible administration of the compatible agent and the 1-OHP are shown in FIG. 10.

(1) No medicine was added (control).

(2) Only the 1-OHP was added at a second day.

(3) A large amount of compatible agents were added at a first day (1 $\mu$g/l of the cisplatin, 10 $\mu$g/ml of the 5-FU, 0.05 $\mu$g/ml of the adriamycin and 1 $\mu$g/ml of the etoposide, and for the comparison purpose, 0.05 $\mu$g/ml of the vincristin and 0.06 $\mu$g/ml of the vindecin). The adding amount of the irinotecano was fixed to 10 $\mu$g/ml, and the addition amount of the 1-OHP was 5 $\mu$g/ml.

(4) A small amount of compatible agents were added at a first day (0.5 $\mu$g/ml of the cisplatin, 5 $\mu$g/ml of the 5-FU, 0.01 $\mu$g/ml of the adriamycin and 0.5 $\mu$g/ml of the etoposide, and for the comparison purpose, 0.01 $\mu$g/ml of the vincristin and 0.01 $\mu$g/ml of the vindecin). The adding amount of the irinotecane was fixed to 10 $\mu$g/ml, and the addition amount of the 1-OHP was 1 $\mu$g/ml.

(5) The 1-OHP and a large amount (the same as that of the above item (3) and so forth in the following items) of the compatible agents were simultaneously added at a first day.

(6) The 1-OHP and a small amount (the same as that of the above item (4) and so forth in the following items) of the compatible agents were simultaneously added at a first day.

(7) The 1-OHP was added at a first day and a large amount of the compatible agents were added at a second day.

(8) The 1-OHP was added at a first day and a small amount of the compatible agents were added at a second day.

(9) The 1-OHP was added at a first day and a large amount of the compatible agents were added at a third day.

(10) The 1-OHP was added at a first day and a small amount of the compatible agents were added at a third day.

(11) The l-OHP was added at a first day and a large amount of the compatible agents were added at a fourth day.

(12) The l-OHP was added at a first day and a small amount of the compatible agents were added at a fourth day.

(13) A large amount of the compatible agents were added at a first day and the l-OHP was added at a second day.

(14) A small amount of the compatible agents were added at a first day and the l-OHP was added at a second day.

(15) A large amount of the compatible agents were added at a first day and the l-OHP was added at a third day.

(16) A small amount of the compatible agents were added at a first day and the l-OHP was added at a third day.

(17) A large amount of the compatible agents were added at a first day and the l-OHP was added at a fourth day.

(18) A small amount of the compatible agents were added at a first day and the l-OHP was added at a fourth day.

In the respective experiments, 5% carbonic acid gas was added to the floating liquid which was cultivated for six days at 37° C. The number of extinct cells per a fixed number of cells (1000 cells) were measured after 24 hours (second day), 48 hours (third day), 72 hours (fourth day), 96 hours (fifth day), 120 hours (sixth day) and 144 hours (seventh day) from a first administration of a medicine (first day). The measurement was conducted by taking out a sample from the cultivation liquid, putting the sample on a sample observation plate (ZOG-1, Elecon Kagaku K.K.), observing cells with an inverted microscope of 1500 magnifications equipped with a fluorescence apparatus (Nikon Corporation) and counting the number of the extinct cells per 1000 cells. The counting of the extinct cells were conducted three times per one experiment and its percentage and the standard deviation were calculated.

From these measurement values, the respective compatible efficiencies (OE, the ratio between the expected value and the measurement value) were calculated employing the following Equation ①.

$$OE\ (\%) = A/[C_0 + (B=C_1) + (D-C_2)] \times 100 \quad ①$$

In the Equation, A is a measurement value of the number of the extinct cells at the seventh day obtained by means of the simultaneous administration, $C_u$ is the value (%) of the extinct coils at the seventh day of the control of the above item (1), B is an effect (%) of extinguishing cells for a period in which the cells were exposed to the l-OHP, $C_1$ is an effect (%) of extinguishing cells of the above item (2) for a period the same as that of B, D is an effect of extinguishing cells for a period in which the cells were exposed to the compatible agent, and $C_2$ is an effect (%) of extinguishing cells of the above item (3) for a period the same as that of D.

Figure 11:
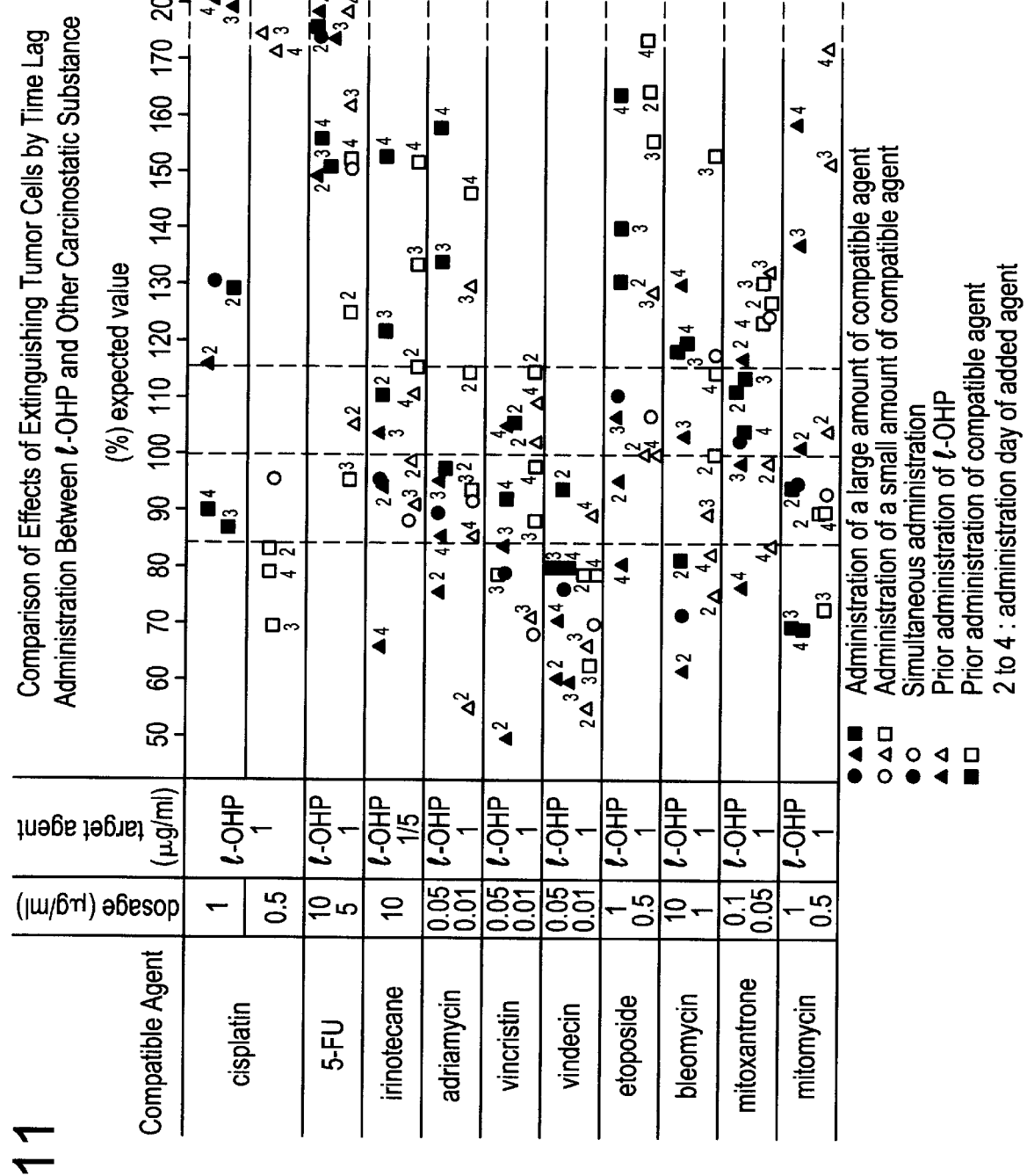
FIG. 11 is a diagram showing calculated values of extinction effects in the respective conditions of compatible administration of compatible agents and l-OP in Example 1.

The calculated values for the respective compatible agents were summarized in FIG. 11.

In FIG. 11, ●, ▲ and ■ designate the administration of the large amount compatible agents, ○, Δ and □ designate the administration of the same amount compatible agents, ● and ○ designate the simultaneous administration, ▲ and Δ designate the preceded administration of the l-OHP. ■ and □ designate the preceded administration of the compatible agent, and the subscripts 2 to 4 designate the day at which the agent was added.

The effects of the respective compatible agents the same as those mentioned earlier were observed. These effects were summarized in Table 1. In the Table ●, ○ and Δ designate the synergistic effect, the additive effect and below the additive effect, respectively.

Comparative Example 1

A target tumor cell was a human leutecyte strain cell (RPMI-8402). The cells were floated in a cultivation bottle (tradename: Sumicron of Sumitomo Bakelite Co., Ltd.) containing a cultivation liquid (PRMI-1640, Gibuko K.K.) containing blood serum of a cow embryo (15%, Gibuko K.K.) which was cultivated for six days in a cultivation apparatus having 15% of carbonic acid gas maintained at 37° C. (taher type, CPD-170 type, Hirasawa K.K.). Medicines to be inspected were added to the cultivation bottle at a concentration close to that clinically employed.

The names and the concentrations of the agents employed in this Example were 100, 50, 10, 5 and 1 μg/ml of OR36-3 (Formula XIV), 0.01 and

TABLE 1

Compatible Effects of l-OHP and Compatible Agent

| Compatible Agent | Dosage of Compatible Agent μg/ml | Simultaneous Administration | Time Lag Administration | | | | | |
|---|---|---|---|---|---|---|---|---|
| | | | Addition Administration of Compatible Agent | | | Addition Administration of l-OHP | | |
| | | | day 2 | day 3 | day 4 | day 2 | day 3 | day 4 |
| cisplatin | 1 | ● | ● | ● | ● | ● | ○ | ○ |
| | 0.5 | ○ | ● | ● | ● | Δ | Δ | Δ |
| 5-FU | 10 | ● | ● | ● | ● | ● | ● | ● |
| | 5 | ● | ● | ○ | ● | ● | ● | ○ | ● |
| irinote- | * | ○ | ○ | ○ | Δ | ○ | ● | ● |
| cane | # | ○ | ○ | ○ | ○ | ● | ● | ● |
| adriamycin | 0.05 | ○ | Δ | ○ | ○ | ○ | ● | ● |
| | 0.01 | ○ | Δ | ● | ○ | ● | ○ | ● |
| vincristin | 0.05 | Δ | Δ | Δ | ○ | ○ | Δ | ○ |
| | 0.01 | Δ | ○ | Δ | ○ | ○ | ○ | ○ |
| vindecin | 0.05 | ○ | Δ | Δ | Δ | ○ | Δ | Δ |
| | 0.01 | Δ | Δ | Δ | ○ | Δ | Δ | Δ |
| etoposide | 1 | ○ | ○ | ○ | Δ | ● | ● | ● |
| | 0.5 | ○ | ○ | ● | ○ | ● | ● | ● |
| bleomycin | 10 | Δ | Δ | ○ | ● | Δ | ● | ● |
| | 1 | ● | Δ | ● | Δ | ○ | ● | ○ |
| mitoxan- | 0.1 | ○ | ● | ○ | Δ | ○ | ○ | ○ |
| trone | 0.05 | ● | ○ | ● | Δ | ● | ● | ● |

TABLE 1-continued

Compatible Effects of 1-OHP and Compatible Agent

| Compatible Agent | Dosage of Compatible Agent μg/ml | Simulta- neous Admini- stration | Time Lag Administration | | | | | |
|---|---|---|---|---|---|---|---|---|
| | | | Addition Administration of Compatible Agent | | | Addition Administration of 1-OHP | | |
| | | | day 2 | day 3 | day 4 | day 2 | day 3 | day 4 |
| mitomycine | 1 | ○ | ○ | • | • | ○ | Δ | Δ |
| | 0.5 | ○ | ○ | • | • | ○ | Δ | ○ |

•: Synergistic Effect
○: Additive Effect
Δ: Below Additive Effect
*Respective Admininstration of 10 μg/ml of irinotecane and of 5 μg/ml of 1-OHP
Respective Administrations of 10 μg/ml of irinotecane and of 1 μg/ml of 1-OHP
1 μg/ml of 1-OHP was administrated in all cases other than irinotecane 0.05 μg/ml of vincristin (VCR) and 5 and 2 μg/ml of cisplatin.

The cultivation liquids were taken out from the respective cultivation bottles as a sample for calculating the number of extinct cells every 24 hours. The percentages, the standard deviations and the OE of the extinct cells were calculated. In accordance with the procedures of Example 1.

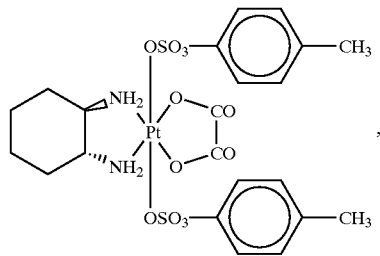

Formula XIV

The effects were investigated employing only the respective amounts of 10 and 5 μg/ml of the OR 36-3 as a single carcinostatic substance. As a result, the extinct effects thereof were 10, 7 and 2% in this turn, and it was apparent that scarce effects could be obtained at an OR-36-3 concentration not less than 10 μg/ml. However, a so-called germination effect could be observed on most of the cells in six hours after the addition of 10 μg/ml. Most of this effect disappeared in one day after the initiation of the cultivation, and this effect which was rarely observed in the inspection of other medicines did not continue to exist after six days as a characteristic feature. It was supposed that the OR 36-3 possessed a function of deriving an internal change (modification) which did not lead a cell to extinction.

Then, for confirming the extinction effect of the high concentration OR 36-3, the extinction effects were measured every 24 hours for six days after the initiation while cultivating the cultivation liquids containing the tumor cells having the respective OR 36-3 concentrations of 100, 50, 10, 5 and 0 (control) μg/ml. The results are shown in FIG. 12.

Figure 12:
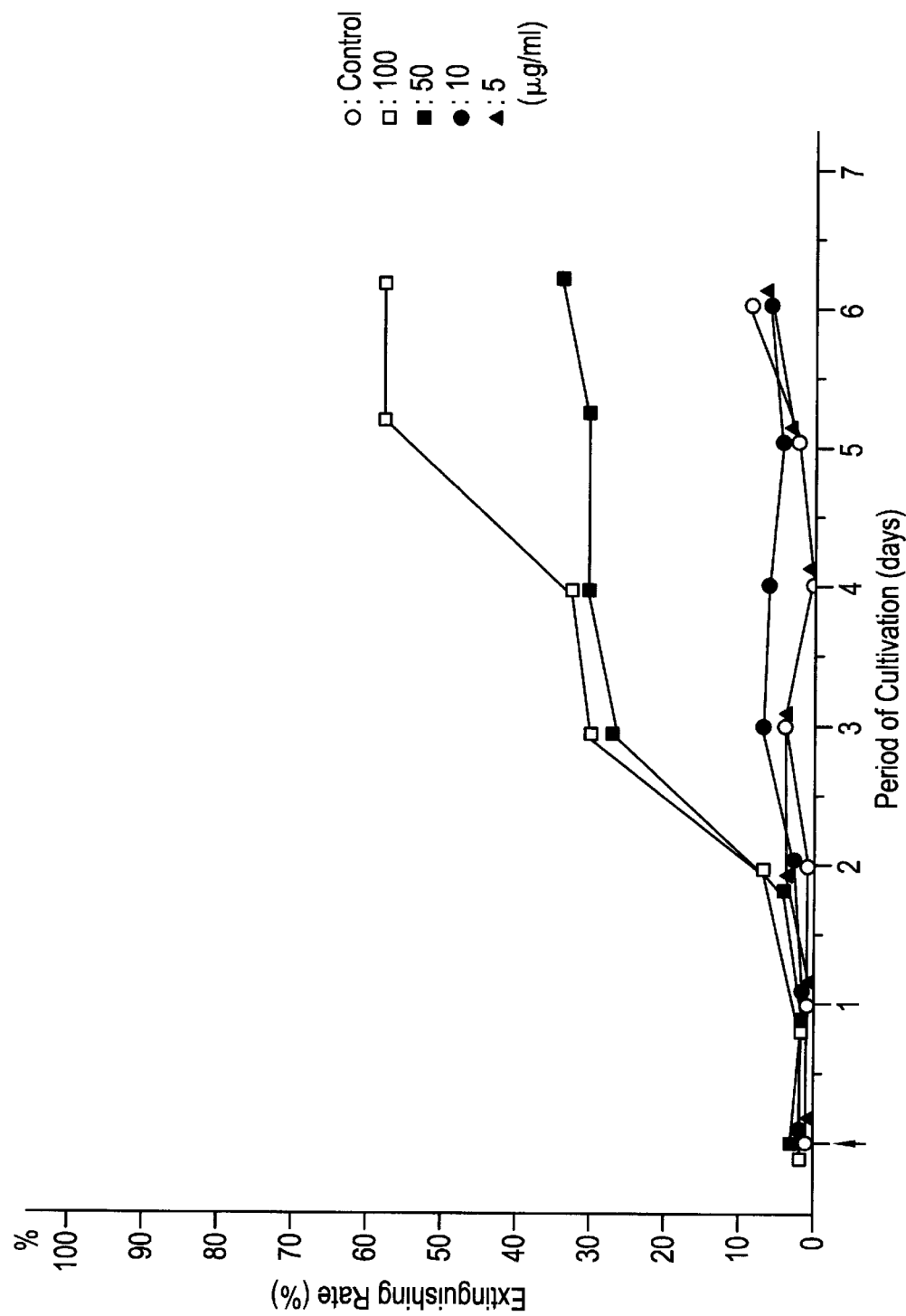
FIG. 12 is a graph showing changes on the time of extinction rates of tumor cells when OR 36-3 is singly employed in Comparative Example 1.

The OR 36-3 exhibited the apparent extinction effect at the concentrations of 50 and 100 μg/ml as shown in FIG. 12.

Example 2

The single vincristin (the concentrations of 0.05 and 0.01 μg/ml) and the four kinds of the compatible administrations of the OR 36-3 and the vincristin (the concentrations of the OR 36-3 and the vincristin were 10 and 0.05 μg/ml, 10 and 0.01 μg/ml, 5 and 0.05 μg/ml and 5 and 0.01 μg/ml) other than the single OR 36-3 (the concentrations of 10 or 5 μg/ml) and the control of Comparative Example 1 were cultivated under the same conditions as those of Comparative Example 1 and their extinction effects were measured. The results were shown in FIG. 13.

Figure 13:
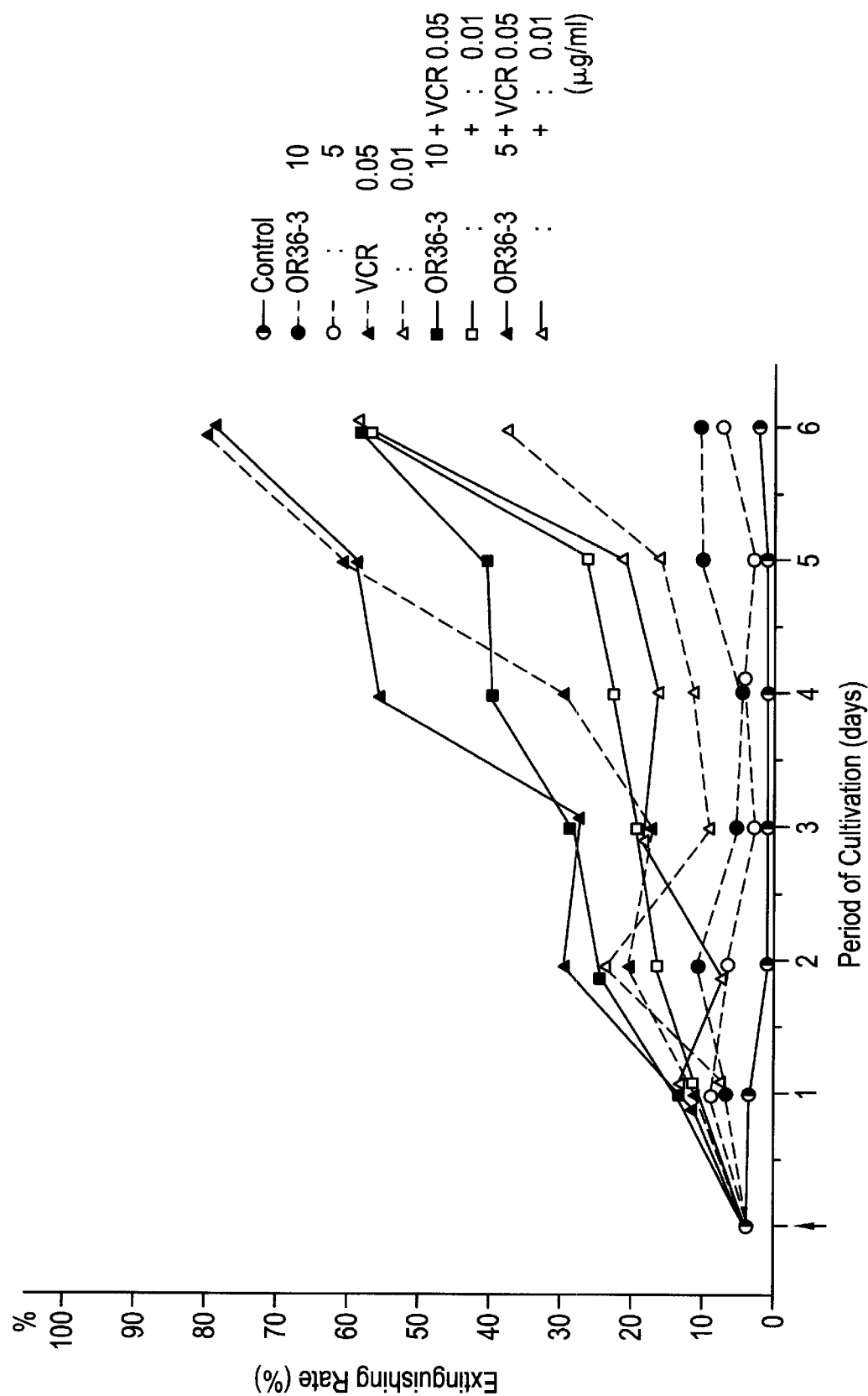
FIG. 13 is a graph showing changes on time of extinction rates of tumor cells when OR 36-3 is compatibly administrated with vincristin in Example 2.

It is clear from FIG. 13 that the OR 36-3 which did not exhibit the apparent extinction effect at the concentration not more than 50 μg/ml exhibited the extinction rate of about 60% after six days even at a concentration of 5 μg/ml (□- and Δ- in FIG. 13) when the OR 36-3 was compatibly administrated with the vincristin. Although the extinction effects of ▲- and ▲. . . in FIG. 13 were similar to those of the single vincristin, the apparent increase of the extinction effects obtained by the compatible administration were produced in the other concentrations and the other lapse of days. This suggests the possibility that the OR 36-3 which does not possess the extinction effect by itself strengthens the extinction effect against cells of another carcinostatic substance by means of a slight modification effect even though the modification of the cells itself by the OR 36-3 does not possess the extinction effect.

Example 3

The extinction rates were measured in accordance with the same procedures of Example 2 except that K 562 parent cells (human bone marrow leukemia) and its cisplatin resistance cells (K652/CDDP) were employed in place of the human leutecyte strain cell employed in Comparative Example 1 and Example 2, and cisplatin was employed in place of the vincristin. The results are shown in FIG. 14.

Figure 14:
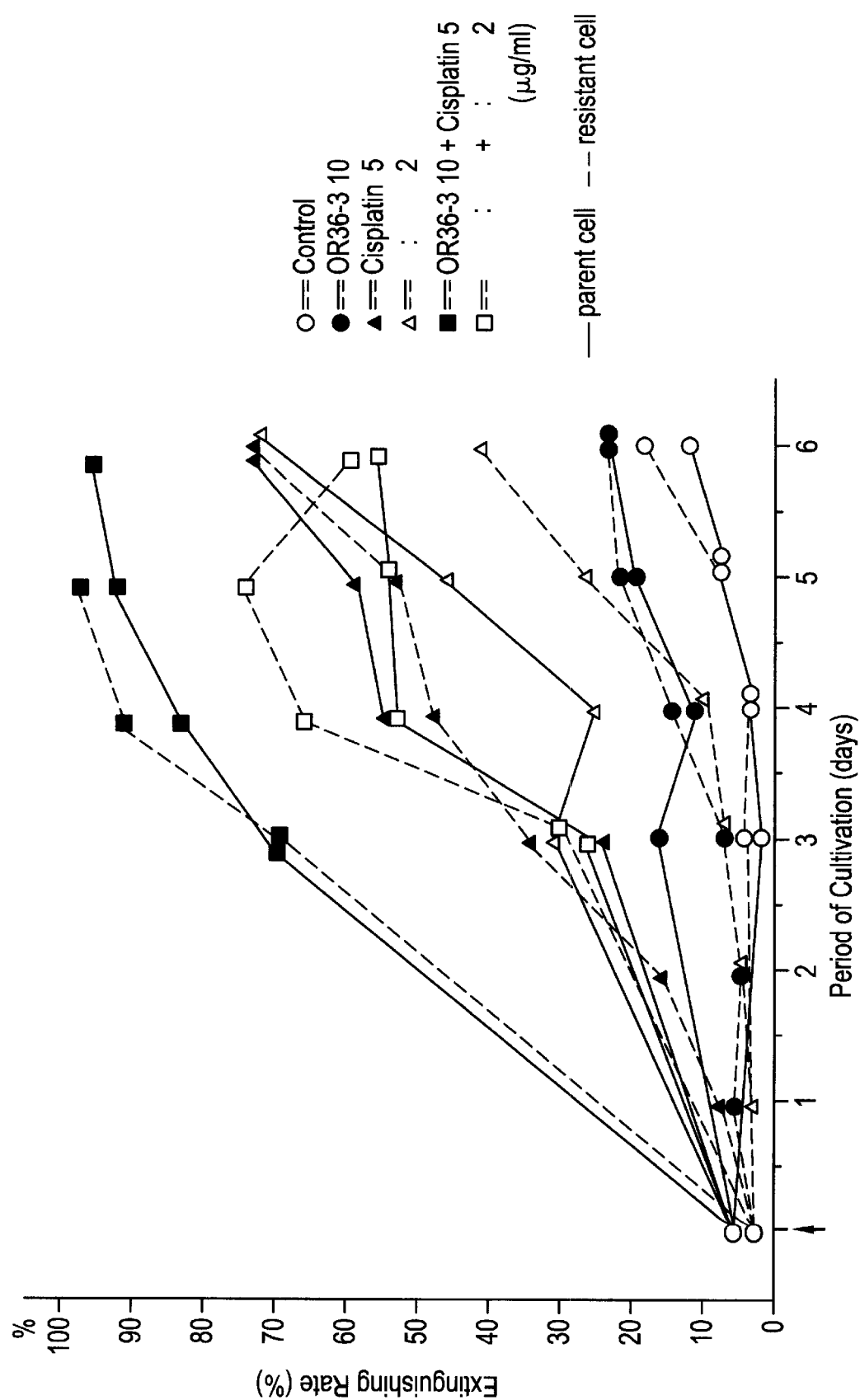
FIG. 14 is a graph showing changes on time of extinction rates of tumor cells when OR 36-3 is compatibly administrated with cisplatin in Example 3.

It is clear from FIG. 14 that the extinction rates against the parent cells and the resistance cells by 5 μg/ml of the cisplatin (▲- and ▲. . .) are substantially the same as each other. However, the extinction rate of the parent cells (Δ-) by 2 μg/ml of the cisplatin was about twice the of the resistance cells (Δ. . . ). In other words, the above cisplatin resistance cells possessed no resistance against 5 μg/ml of the cisplatin and extinguished at a sensitivity the same as that of the parent cells while the cisplatin resistance cells possessed the resistance twice that of the parent cells against the cisplatin and extinguished at a sensitivity the same as that of the parent cells against 2 μg/ml of the cisplatin.

On the other hand, 10 μg/ml of the OR 36-3 possessed scarce effects against the parent cells and the resistance cells. Then, when 5 or 2 μg/ml of the cisplatin was compatibly employed with 10 μg/ml of the OR 36-3, the compatible efficiencies after the six days at the administration of 5 µg/ml were calculated to be 116% and 125% against the parent cells and the resistance cells, respectively, and those after the six days at the administration of 2 µg/ml were calculated to be 66% and 129% against the parent cells and the resistance cells, respectively.

Accordingly, the compatible effects of the OR 36-3 and the cisplatin to the parent cells and to the resistance cells at 5 µg/ml and to the resistance cells at 2 µg/ml were confirmed. This means that the resistance of the cells formed by the cisplatin disappeared by the addition administration of the OR 36-3. In other words, the OR 36-3 of which an amount is insufficient for functioning as a carcinostatic substance can strengthen the effect when compatibly administrated with the cisplatin.

Example 4

After 5 ml of a cultivation liquid (a liquid prepared by adding 15% of blood serum of a cow embryo) containing, as a target cancer cell, $10^6$ cells/ml of human leutecyte strain cells (RPMI-8402) was put into a floating cultivation flash (Sumiron), the cells were cultivated for six days in a cultivation apparatus containing 5% carbonic acid gas at 37° C. To the respective cultivation liquids were added, together with 1 µg/ml of the DAPI, ① the control (no addition of the carcinostatic substance), ② 5 µg/ml of CPT (camptotecin), ③ 10 µg/ml of CPT-11 (iriftecan), ④ 0.06 µg/ml of ADR (adriamycin), ⑤ 0.05 µg/ml of DNR (daunomycin), ⑥ 1 µ/ml of etoposide, ⑦ 20 µg/ml of MST-16 (sopsoxane), ⑧ 1 µg/ml of m-AMSA (amscarine), ⑨ µg/ml of Act-D (actinomycin D), ⑩ 0.1 µg/ml of mitoxantrone. ⑪ 20 µg/ml of 5-FU, ⑫ 10 µg/ml of Ara-C (cytosinarabinoside) ⑬ 50 µg/ml of hydroxyurea, ⑭ 2 µg/ml of Aphidicolin, ⑮ 10 µg/ml of MTX (mesotroxate), ⑯ 0.05 µg/ml of VCR (vincristin), ⑰ 0.05 µg/ml of VDS (vindecin). ⑤ µg/ml of cisplatin, ⑱ 10 µg/ml of bleomycin, ⑳ 10 µg/ml of MMC (mitomycin C) and (21) 5 µg/ml of cyclophospamide (endoxane). The samples were sampled from the respective cultivation liquids after one hour, four fours, 24 hours and then every 24 hour from the initiation of the cultivation. The samples were evaluated in accordance with the procedures of the preceding Examples. The results are shown in a graph of FIG. 15.

Figure 15:
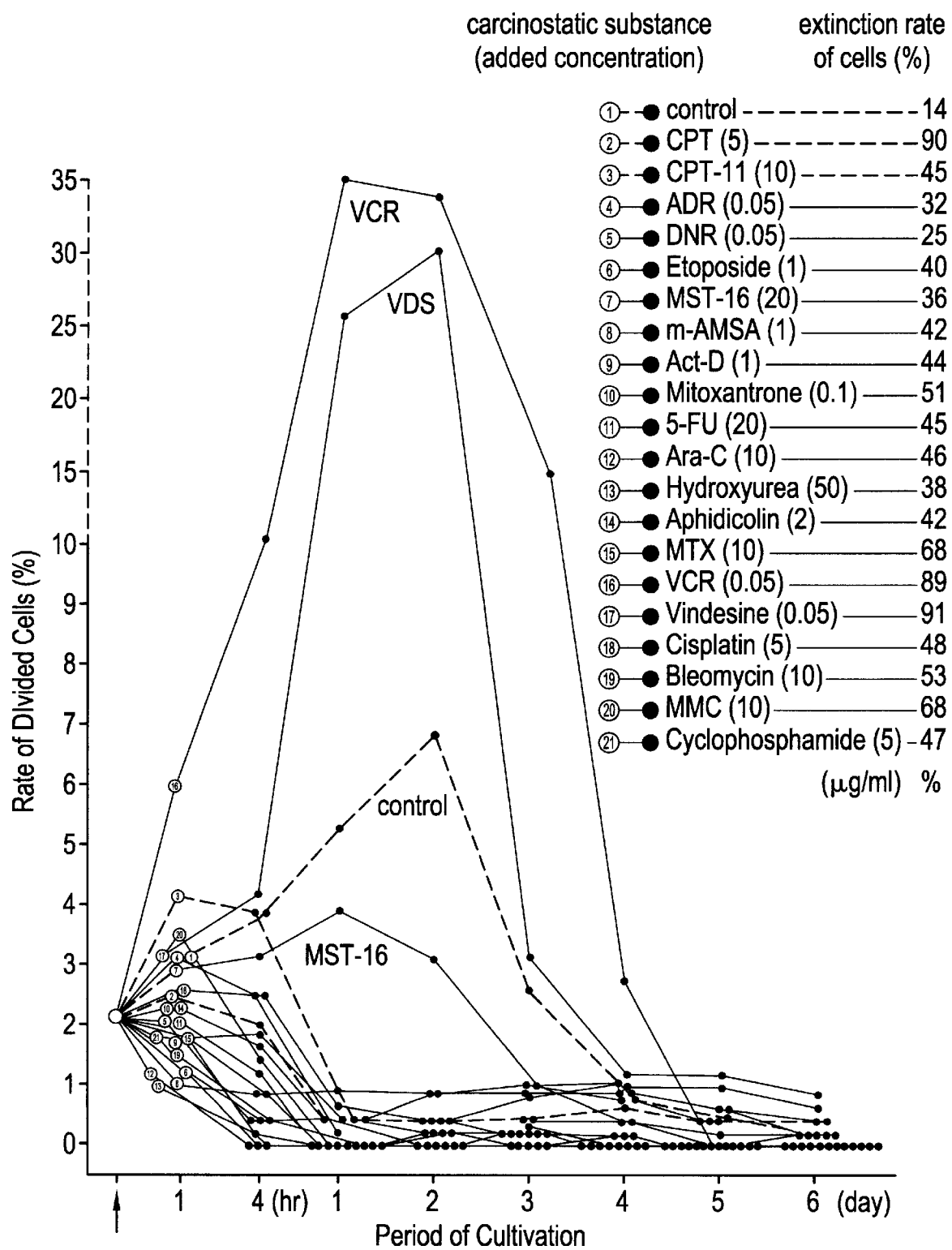
FIG. 15 is a graph showing a relation between a cultivation time and a percentage of divided cells in an inspection test for carcinostatic substances in Example 4.

As shown in FIG. 15, among the 20 carcinostatic substances, the remarkable increases of the numbers of the divided cells were observed in ⑯ VDR and ⑰ VDS compared with the control. The increase of the number of the divided cells was momentarily observed in ⑦ MST-16, but the said number was steeply decreased after the second day, and on the sixth day all the appearance rates of the divided cells of the 20 carcinostatic substances became below 1%.

The appearance rates of the divided cells of the all the carcinostatic substances except for these three carcinostatic substances became below 1% in one day after the initiation of the cultivation and on the sixth day the cell division was scarcely inspected.

From these results, it is apparent that almost all the carcinostatic substances (excluding ⑱) largely decreased the numbers of the divided cells in one day after the initiation of the cultivation compared with the control, and in other words it means that the said substances largely decreased the number of the cancer cells entering into the cell division, and accordingly it clarifies that the respective carcinostatic substances exhibited the anti-tumor properties.

In the conventional test tube method and animal method, even a prediction cannot be presented whether a carcinostatic substance under inspection possesses an anti-tumor property in one or two days after the initiation of the cultivation. In this Example, the anti-tumor property of the carcinostatic substance to be inspected or the effectiveness of the carcinostatic substance can be accurately inspected only by knowing the percentage, as apparent from the foregoing description.

The ratio of the divided cells increased after the initiation of the cultivation in the above mentioned three carcinostatic substance ⑦, ⑯ and ⑰. In accordance with the microscope observation, all the division phases of the said divided cells were the division prophase and the division metaphase, and no cells under the the division anaphase and the division telophase were observed. This suggests that the cells under the division prophase reached to the following division metaphase but the successive progress was depressed, and in other words the cell division stopped at the division anaphase.

As mentioned, when the process of observing the cell division using the fluorescence dye is employed, the mechanism of the cell division can be clarified and further important information can be obtained because the morphosis changes of the nucleus can be monitored.

What is claimed is:

1. A process for the treatment of cancer in a patient comprising compatibly administering to said patient a synergistically effective amount of irinotecane and subsequently with a synergistically effective amount of cis-oxalato (1R, 2R-diaminocyclohexane) Pt (II) and wherein the cancer is sensitive to the combination.

2. The process of claim 1 wherein said cis-oxalato (1R, 2R-diaminocyclohexane) Pt (II) is administered about one day after said irinotecane.

3. The process of claim 1 wherein said cis-oxalato (1R, 2R-diaminocyclohexane) PT (II) is administered about two days after said irinotecane.

4. The process of claim 1 wherein said cis-oxalato (1R, 2R-diaminocyclohexane) Pt (II) is administered about three days after said irinotecane.

* * * * *